United States Patent [19]

Kubela et al.

[11] 4,286,095
[45] Aug. 25, 1981

[54] 4-ARYLPIPERIDINE DERIVATIVES

[75] Inventors: Rudolf Kubela, Cote St. Luc; Philip D. Edwards, Chateauguay; Lisa A. Hughes, Ville de Lery, all of Canada

[73] Assignee: Canada Packers Inc., Toronto, Canada

[21] Appl. No.: 34,972

[22] Filed: May 1, 1979

Related U.S. Application Data

[63] Continuation-in-part of Ser. No. 876,702, Feb. 10, 1978, abandoned, which is a continuation-in-part of Ser. No. 711,886, Aug. 5, 1976, abandoned.

[51] Int. Cl.$^3$ .............................................. C07D 211/52
[52] U.S. Cl. .................................... 546/213; 546/218; 546/217; 424/267
[58] Field of Search ....................... 546/217, 218, 213; 424/267

[56] References Cited

U.S. PATENT DOCUMENTS

| | | | |
|---|---|---|---|
| 3,445,474 | 5/1969 | Carabateas | 546/218 |
| 4,048,314 | 9/1977 | Kubela et al. | 546/217 |

FOREIGN PATENT DOCUMENTS 1049564  11/1966  United Kingdom ..................... 546/217

OTHER PUBLICATIONS

R. E. Lyle et al., Jour. Org. Chem., vol. 30(2) (1965), pp. 394–396.
V. Petrow et al., Jour. Pharm. Pharmacol., vol. 14(5) (1962), pp. 306–314.
Schmidle et al., Jour. Am. Chem. Soc., vol. 78, Jan. 20, 1956, pp. 425–428.

*Primary Examiner*—Norma S. Milestone
*Attorney, Agent, or Firm*—Bacon & Thomas

[57] ABSTRACT

A 4-phenyl piperidine having the formula:

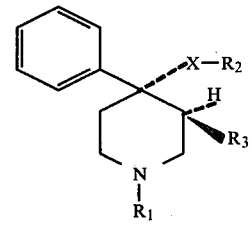

wherein $R_1$ is a straight chain lower alkyl group; $R_2$ is —COCH$_3$, —COC$_2$H$_5$ or

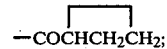

$R_3$ is —OCOCH$_3$, —OCOC$_2$H$_5$, —OCO -cycloalkyl, or —OCOC$_6$H$_4$—Z; wherein Z is hydrogen, lower alkyl, lower alkoxy or chlorine, and X is oxygen: or an addition salt thereof with a pharmaceutically acceptable organic acid or inorganic acid. The compounds have have found to have, inter alia, stimulatory effects on the central nervous system which is indicative of their use as antidepressants in humans.

10 Claims, No Drawings

4-ARYLPIPERIDINE DERIVATIVES

This is a continuation-in-part application of U.S. Ser. No. 876,702 filed on Feb. 10, 1978, which in turn is a continuation-in-part application of U.S. Ser. No. 711,886 filed on Aug. 5, 1976, which two previous applications have now been abandoned.

The present invention relates to novel 4-arylpiperidine derivatives, processes for the production thereof and compositions containing same.

DESCRIPTION OF THE INVENTION

According to one aspect of the present invention there are provided novel 4-phenyl-piperidine derivatives of the general formula I:

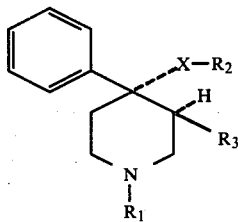

I wherein $R_1$ represents straight or branched chain lower alkyl or lower aralkyl;

$R_2$ represents a lower straight or branched chain alkyl which may carry a lower alkoxy; cycloalkyl; lower alkenyl; lower alkynyl; phenyl optionally mono- or di-substituted by halogen, lower alkyl or lower alkoxy; or a lower acyl of formula —CO—R wherein R is a lower straight or branched chain lower alkyl, cycloalkyl or phenyl;

$R_3$ represents hydroxy or an ester derivative thereof;

X represents oxygen or sulphur, as well as addition salts thereof with organic or inorganic acids.

Since the compounds of formula I have chiral centres at $C_3$ and $C_4$, it will be obvious to one skilled in the art that these compounds may be present as optical isomers. The connotation of the general formulae presented herein is to include all such isomers either separated or in d,l mixtures.

Also, it will be noted that substituent groups X—$R_2$ and $R_3$ are always trans to each other in the compounds of formula I.

Throughout this specification the terms "lower alkyl", "lower alkoxy", "lower acyl", and "lower alkynyl" refer to such groups having at most six, and preferably at most four, carbon atoms. Examples of lower alkyl groups include methyl, ethyl, isopropyl, propyl, butyl, isobutyl, sec. and tert. butyl, pentyl, isopentyl, neopentyl and the various hexyl isomers; lower alkoxy includes methoxy, ethoxy and isopropoxy. Lower alkynyl includes ethynyl and 2-propynyl and lower alkenyl includes vinyl and 2-propenyl. Lower acyl groups include acetyl, propionyl, etc. The term lower aralkyl refers to such groups having at most six, preferably at most four, carbon atoms in the alkyl moiety, examples thereof being phenyl-lower-alkyl, phenethyl, but especially benzyl, and naphthyl-lower-alkyl such as 2-naphthyl-methyl.

The term cycloalkyl as used herein means cyclopropyl, cyclobutyl, cyclopentyl, cyclohexyl or cycloheptyl.

A restricted class of compounds of formula I are those wherein $R_1$ represents a straight or branched chain lower alkyl; or lower phenylalkylene;

$R_2$ represents straight or branched chain lower alkyl which may carry a lower alkoxy; cyclohexyl; phenyl, optionally mono- or di-substituted by halogen; lower alkyl; lower alkoxy; lower acyl of formula —COR where R is a lower alkyl; cycloalkyl; phenyl which may be mono- or disubstituted with lower alkyl, lower alkoxy or halogen;

$R_3$ represents hydroxy, or an ester derivative thereof of formula —OCO—$R_5$ where $R_5$ is straight or branched chain lower alkyl optionally substituted by lower acyloxy or chlorophenoxy; cycloalkyl, lower alkenyl, diphenyl methyl; 2- or 3-furyl or phenyl, optionally substituted by amino, halogen, nitro up to three lower alkoxy groups, $CF_3$, an ester moiety of formula —OCO-lower alkyl, lower acylamino; and X represents oxygen or sulphur, especially oxygen; as well as acid salts thereof with organic or inorganic acids.

A preferred class of compounds according to the present invention on account of their advantageous pharmacological activity are those compounds of formula I above wherein $R_2$ and $R_3$ are such that positions 3 and 4 carry ester moieties (the same or different), especially those of formula —OCO—R wherein R is lower alkyl, cycloalkyl or phenyl, optionally substituted by lower alkyl, lower alkoxy or halogen.

An exemplary class of such compounds of formula I are those wherein $R_1$ represents a straight chain lower alkyl group;

$R_2$ is a moiety of formula —COR, wherein R is a straight chain, lower alkyl group, a cycloalkyl group or a phenyl group;

$R_3$ is a moiety of formula —OCO—$R_5$ wherein $R_5$ is
(i) an unsubstituted, straight chain, lower alkyl group;
(ii) a branched chain, lower alkyl group substituted with a chlorophenoxy group,
(iii) a diphenylmethyl group,
(iv) a cycloalkyl group,
(v) a 2-furyl or 3-furyl group, or
(vi) an unsubstituted phenyl group or a phenyl group substituted with up to two lower alkyl groups, up to three lower alkoxy groups, a halogen atom, a trihalomethyl group or a lower alkyl carbonyloxy group; and X represents oxygen; as well as pharmaceutically acceptable acid addition salts thereof with an organic or inorganic acid.

Of particular note are compounds of formula:

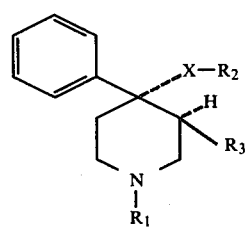

II wherein X represent oxygen;
$R_1$ represents a straight chain lower alkyl;
$R_2$ represents —$COCH_3$, —$COC_2H_5$ or

—COCHCH₂CH₂;

and $R_3$ represents —OCOCH₃, —OCOC₂H₅, —OCO-cycloalkyl or —OCOC₆H₄—Z wherein Z is hydrogen; chlorine, lower alkyl or lower alkoxy; and pharmaceutically acceptable acid additions salts thereof with organic or inorganic acids.

The present invention in a further aspect, provides processes for producing compounds of formula I. In one process, the novel compounds of the present invention may be prepared from an epoxide of formula IV:

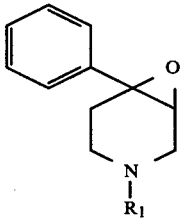

wherein $R_1$ is defined above for formula I.

The compounds of formula IV are converted into the compounds of formula I by a reaction involving cleavage of the epoxide ring, the choice of cleavage agent being determined primarily by the —X—$R_2$ moiety desired in the product of formula I. For example, (A) When X=O and $R_2$=lower alkyl The selected epoxide of formula IV is reacted with the corresponding alcohol of formula:

HO—$R_2$ in the presence of at least one molar equivalent of a strong acid. The reaction may be conducted in a solvent, which may be constituted by an excess of the alcohol reactant. Preferred alcohols are methanol, ethanol and isopropanol.

(B) When X=O and $R_2$=lower acyl, cycloalkylcarbonyloxy

The selected epoxide of formula IV is reacted with the corresponding carboxylic acid of formula:

HO—CO—$R_2$ in the presence of at least one molar equivalent of a strong acid. Again a solvent may be used and this may be constituted by an excess of the carboxylic acid reactant.

Preferred acids include acetic acid and propionic acid.

In these two process embodiments, the strong acid may be p-toluenesulphonic acid, sulphuric acid and hydrochloric acid.

Reaction is usually effected by heating, conveniently at the reflux temperature of the reaction medium.

(C) When (i) X=S and $R_2$=lower alkyl or phenyl optionally substituted as defined above;

(ii) X=O and $R_2$=phenyl

The selected epoxide of formula IV is treated with the corresponding thiol of formula:

HS—$R_2$ or phenol of formula:

HO—$R_2$ in a solvent, such as ethylene glycol and in the presence of a base conveniently alkali metal hydroxides such as sodium hydroxide and potassium hydroxide.

(D) An alternative process for producing those compounds of formula I wherein X=O, involves reacting a diol of formula:

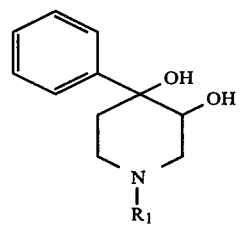

wherein $R_1$ is defined above with the corresponding carboxylic acid reactive derivative such as the acid chloride or anhydride. In some instances, depending inter alia on the starting diol and the esterifying reagent, it is possible to convert both hydroxy groups into ester moieties. In such cases, use of at least two molar equivalents of the esterifying agent will result in the diester having similar ester moieties at the 3 and 4 positions.

As will be appreciated, compounds of formula IV wherein $R_1$ is hydrogen are secondary amines and in certain instances may be involved in undesirable competing reactions involving cleavage of the epoxide ring with the selected cleaving agent. This is only likely to occur to any significant extent when the cleaving agent is bulky in nature, and the possibility of said undesirable reactions occurring may be reduced by effecting the reaction at a lower temperature than in the other instances, for example, a temperature below 100° C. compared with a temperature of between 100°-200° C., usually about 150° C. However, in such cases, it is preferred to produce compounds of formula I but wherein $R_1$ is hydrogen by cleaving the epoxide ring of a corresponding compound of formula I wherein $R_1$ is an amine protecting group, such as acyl, with the desired cleaving agent and subsequently convert group $R_1$ to hydrogen in a known manner, for example, by hydrolysis with acid or base. Such N-unsubstituted compounds may be utilized as starting materials in producing desired compounds of formula I.

Moreover, compounds of formula I may in general be used as intermediates in the obtainment of other compounds of formula I. For example, those compounds of formula I wherein $R_1$ is alkyl may be obtained from the compound of formula I wherein $R_1$ is hydrogen by simple alkylation by known standard procedures using, for example, alkylhalides. Likewise, compounds of formula I wherein $R_3$ is a hydroxyl-group-derivative may be obtained from the corresponding free hydroxyl compound, for example, by esterification in known manner. This method may be used to produce compounds having different ester moieties at positions 3 and 4.

If the mixture of isomers obtained as the product in any specific reaction is not utilizable in that form due to the undesirable presence of one or more isomers, the isomers may be separated by standard techniques generally utilizing differences in the physical and/or chemical properties between the isomers, such as relative solubilities, differing recrystallization rates and differing retention rates in chromatographic separation processes, such as column chromatography.

The 4-phenylpiperidines of formula I form acid addition salts with various inorganic or organic acids and such salts are included within the scope of the present invention. Of special interest are the pharmaceutically acceptable acid addition salts which are usually more convenient to handle than the free compounds of formula I. Acids which form such salts include hydrochloric acid, hydrobromic acid, sulfuric acid, phosphoric acid, nitric acid, acetic acid, maleic acid, fumaric acid, tartaric acid, succinic acid, citric acid, camphorsulfonic acid, ethanesulfonic acid, ascorbic acid and lactic acid.

Of the starting materials, namely, the 3,4-epoxypiperidines of formula IV:

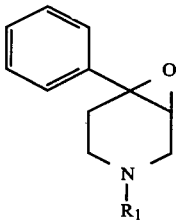

IV the compound wherein $R_1$ is methyl is known being described in the literature along with its preparation. Other compounds of formula IV wherein $R_1$ as defined above may be prepared in an analogous manner. For example, they may be obtained by the epoxidation of compounds of formula V:

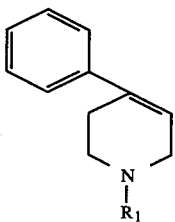

V wherein $R_1$ is as defined above.

The epoxidation may be effected in several ways for example:

(1) oxidation using a percarboxylic acid according to the following scheme:

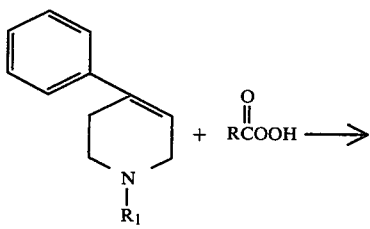

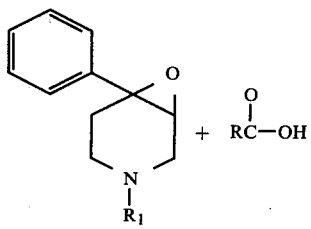

wherein $R_1$ is acyl, or (2) from a halohydrin in the presence of a base according to the following scheme:

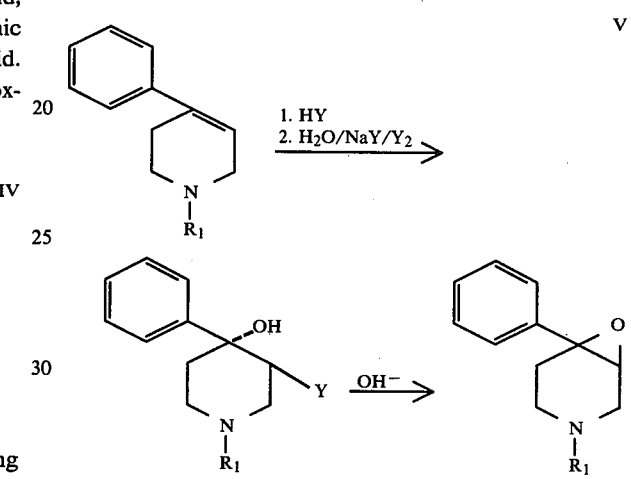

V wherein $R_1$ is hydrogen, i.e., the nitrogen is basic in character and Y is halogen.

However, it will be obvious to the skilled chemist that the actual procedure used for the epoxidation must be chosen to avoid the possibility of undesirable side reactions.

It will be readily apparent that in general the said epoxy compounds where $R_1$ is other than hydrogen may be obtained from the corresponding epoxy compounds where $R_1$ is hydrogen by alkylation, etc. in known manner of the latter compounds.

Some of the 4-aryl-1,2,3,6-tetrahydropyridines of formula V, namely, those of formula VI:

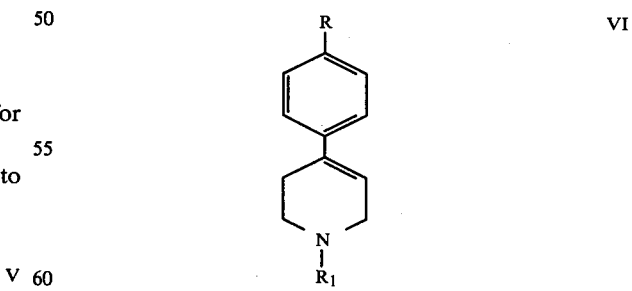

VI wherein R is hydrogen or methyl and $R_1$ is various hydrocarbon moieties are known compounds being described along with a process for their preparation, for example, in J.A.C.S. (1956) Vol. 78, p. 425–428. Any novel compounds of formula V may be prepared in a similar manner to the known compounds with, of course, the appropriate choice of starting materials.

An alternative process for preparing these compounds comprises reacting formaldehyde, an appropriately substituted α-methylstyrene and an amine according to the following scheme:

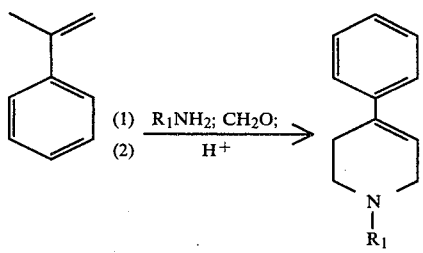

wherein $R_1$ is as defined above, and amine $R_1NH_2$ is in the form of an acid addition salt.

Again, starting compounds wherein substituent $R_1$ is hydrogen may be converted into compounds wherein $R_1$ is other than hydrogen by standard known procedures as described above.

Of the 4-phenylpiperidine-3,4-diols of formula III some are known, for example, 1-methyl-4-phenylpiperidine-3,4-diol (J.O.C. 30, 394–396 [1965] R. E. Lyle and W. E. Kruger). Any novel compounds of formula III may be prepared in a similar manner to the said known compound with, of course, the appropriate choice of starting materials.

The novel 4-phenylpiperidines of the present invention possess useful biological properties and generally they have activity, as determined by standard tests, indicative of at least one of the following activities; antidepressant, antiaggresive, diuretic, antiparkinson, bronchodilator and antiarthritis, antithrombotic and muscular relaxant activities. For example, compounds of restricted formula I when administered to mice have generally been found to have a significant stimulatory effect on the central nervous system indicative of ultimate antidepressant and similar clinical use in humans. Moreover, this activity is associated with an acceptable toxicity index.

The following table summarizes the results obtained when some compounds of preferred formula I above were evaluated for antidepressant activity using standard test procedures (ref. R. A. Turner, P. Hebborn, Screening Methods in Pharmacology, Vol. II, Acad. Pr., N.Y., London, 1971, page 214). Reserpine was used to induce ptosis and the test compounds were administered per os. The results obtained in the same test for the known antidepressant imipramine are included as a comparison. Response values >3 are considered pharmacologically significant.

| | Compound | Dose Mg/kg | Response |
|---|---|---|---|
| A | 1-methyl-3-acetoxy-4-(propionyloxy)-4-phenyl-piperidine | 25<br>1<br>0.5 | 8<br>8<br>5 |
| B | 1-methyl-3-ethylcarbonyloxy-4-(p-chlorophenyloxy)-4-phenyl-piperidine | 50<br>10<br>5 | 8<br>7<br>5 |
| C | 1-methyl-3-hydroxy-4-phenylthio-4-phenyl-piperidine | 50<br>10<br>5 | 10<br>6<br>4 |
| D | 1-methyl-3-cyclopropylcarbonyloxy-4-ethylcarbonyloxy-4-phenylpiperidine | 0.05 | 4 |
| E | 1-methyl-3-cyclobutylcarbonyloxy-4-ethylcarbonyloxy-4-phenylpiperidine | 0.25 | 5 |
| F | 1-methyl-3-cyclohexylcarbonyloxy-4-ethylcarbonyloxy-4-phenylpiperidine | 0.25 | 5 |
| | Imipramine | 25<br>5 | 4<br>1 |

It can be seen that the antidepressant activity of the compounds of the present invention compares very favourably with the known antidepressant Imipramine. This is especially so for the compounds of formula I having an ester moiety at positions 3 and 4 as exemplified by Compound A above.

In other similar screening tests, the following results were obtained:

| Diuretic Activity (PO) | | |
|---|---|---|
| | Base (Mg/kg) | Response* |
| Compound A | 5 | 4.3 |
| Compound E | 10 | 2.9 |
| Compound F | 5 | 3.0 |
| Hydroflurmethiazide | 5 | 2.6 |

*Responses >2 are considered pharmacologically significant.

| Bronchodilatory Activity (in vitro - PO) | | |
|---|---|---|
| | Base (Mg/kg) | Response** |
| Compound B | 50 | + |
| Aminophylline | 200 | + |

**Responses are positive (+) or negative (−).

The present invention further provides in another of its aspects a pharmaceutical composition comprising as an essential active ingredient at least one active compound of formula I or a pharmaceutically acceptable acid addition salt thereof in association with a pharmaceutically acceptable carrier therefor.

The compositions of the present invention are preferably administered orally, rectally or parenterally. Advantageously, the composition is in a dosage unit form appropriate to the desired mode of administration. For example, the dosage unit may be a tablet, capsule, pill, powder, packet, granule, wafer, elixir, suppository, or a measured quantity of a suspension, solution, a syrup or segregated multiples of the foregoing. The term "dosage units form" as used in the specification and claims refers to physically discrete units suitable as unitary dosages for human subjects and animals, each unit containing a predetermined quantity of active material calculated to produce the desired therapeutic effect in admixture, or otherwise in association, with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

Usually the compositions of this invention contain the active ingredient in an amount of at least 0.5% by weight based on the total weight of the composition and not more than 95% by weight. Conveniently, the compositions of the invention when in dosage unit form contain 0.5 mg. to 100 mg., and more conveniently from 5 mg. to 50 mg., of the active ingredient of Formula I.

The compositions of the present invention will normally consist of at least one compound of formula I, advantageously a compound of formula IIa, or a pharmaceutically acceptable acid addition salt thereof, admixed with a carrier, or diluted by a carrier, or enclosed or encapsulated by a carrier in the form of a capsule, sachet, catchet, paper or other container. A carrier which serves as a vehicle, excipient or diluent medium for the therapeutically active ingredient may be a solid, semi-solid or a sterile liquid.

Some examples of the carriers which may be employed in the pharmaceutical compositions of the invention are lactose, dextrose, sorbitol, mannitol, starches such as wheat, corn, or potato starch, gum acacia, calcium phosphate, liquid paraffin, cocoa butter, oil of theobroma, alginates, tragacanth, gelatin, syryp B.P., methyl cellulose, polyoxethylene sorbitan monolaurate, and methyl and propyl hydroxybenzoates. The choice of carrier is determined by the preferred form of administration the solubility of the compound and standard pharmaceutical practice, all as more clearly set forth in "Remington's Practice of Pharmacy" by E. W. Martin and E. F. Cook, a well-known reference work in this field. In the case of tablets, a lubricant may be incorporated to prevent sticking and binding of the powdered ingredients in the dies and on the punch of the tabletting machine. For such purpose, there may be employed, for example, talc, aluminum, magnesium or calcium stearates or polyethylene glycols "Carbowaxes" (Registered Trade Mark) of suitable molecular weight.

The pharmaceutical compositions of this invention may contain, in addition to the active 4-arylpiperidine ingredient, one or more other physiologically active ingredients which elicit desirable complementary effects.

Examples of suitable pharmaceutical compositions according to the present invention are presented below for the purposes of facilitating a better understanding of this aspect of the invention.

COMPOSITIONS

Composition 1

For oral administration, sugar coated tablets may have the following composition, the tablets being made up in the usual manner.

| Ingredient | Amount (mg) |
| --- | --- |
| 1-Methyl-3-acetoxy-4-(propionyloxy)-4-phenyl-piperidine | 10 |
| Lactose | 60 |
| Starch | 50 |
| Sugar | 75 |
| Talc | 5 |
| Gum Arabic | 5 |

Composition 2

Capsules, made up in the usual manner may have the following composition:

| Ingredient | Amount (mg) |
| --- | --- |
| 1-Methyl-3-propionyloxy-4-(p-chlorophenyloxy)-4-phenyl-piperidine | 5 |
| Lactose | 145 |

Composition 3

Tablets for oral administration may also be made up according to the known procedure described below:

| Ingredient | Amount (mg) |
| --- | --- |
| 1-methyl-3-cyclopropylcarbonyloxy-4-ethylcarbonyloxy-4-phenylpiperidine | 0.175 |
| Lactose | 0.502 |
| Starch | 0.122 |
| Dextrin (20% solution) | q.s. |
| Stearic acid | 0.004 |
| Magnesium stearate | 0.002 |

It will be appreciated that the above specific compounds may be replaced by other active compounds of the present invention.

As indicated hereinbefore, it has been found in accordance with the present invention that the compounds of Formula I possess useful biological properties in that such compounds possess the inherent applied use characteristics of exerting for example, antidepressants on the central nervous system. Compounds possessing such activity may have very valuable therapeutic utility as potential medicaments in the form of pharmaceutical compositions in eliciting advantageous central nervous system effects when administered to humans and animals. Accordingly, central nervous system effects, on humans and animals, may be elicited by administering a therapeutically effective dose of one or more of the active compounds of Formula I, (preferably a compound of formula II) wherein CNS symptom being treated, the age, health and weight of the recipient, the extent of the symptom, kind of concurrent treatment, if any, and the precise nature of the effect desired. In practise, based upon standard pharmacological animal studies, particularly in mice, it has been found that the administration of doses of 1 to 100 mg of the active compounds of this invention per kg of animal body weight will usually elicit the aforementioned CNS, especially antidepressant effect(s) normally without producing any marked side effects.

The present invention will be further described with reference to, but not limited by, the following specific examples.

EXAMPLE 1

4-(p-Chlorophenoxy)-3-hydroxy-1-methyl-4-phenyl piperidine and its hydrochloride 20 Ml of 10% sodium hydroxide solution was added to a solution of 6.45 g (0.05 mole) of p-chlorophenol in 40 ml of ethylene glycol and the resulting solution stirred at room temperature for five minutes. 3.8 G (0.02 mole) of 3,4-epoxy-1-methyl-4-phenylpiperidine was added with stirring to the above solution and the resulting solution was heated at 120° C. on an oil bath for 18 hours.

The solid which resulted was filtered, washed with water and dissolved in methylene chloride. The resulting solution was dried over sodium sulfate and concentrated in vacuo to give 3.6 g of a white solid. Recrystallization of this solid from ethyl acetate gave 4-(p- chlorophenoxy)-3-hydroxy-1-methyl-4-phenyl-piperidine as colourless crystals having a melting point of 164°–5° C.

The corresponding hydrochloride was prepared in the usual manner and had a melting point of 221° C.

Elementary Analysis: $C_{18}H_{20}NO_2Cl$; Calc. C: 68.02; H: 6.34; N: 4.41; Found C: 68.10; H: 6.62; N: 4.34.

EXAMPLE 2

3-Acetoxy-1-methyl-4-(m-methylphenoxy)-4-phenyl piperidine and its hydrochloride 2.12 Ml (0.015 mole) of triethylamine was added to a solution of 3.0 g (0.010 mole) of 3-hydroxy-1-methyl-4-(m-methylphenoxy)-4-phenylpiperidine in 30 ml of dry methylene chloride and the solution cooled in an ice-bath. This solution was stirred and 1.08 ml (0.015 mole) of acetyl chloride was added dropwise. The reaction mixture was stirred at room temperature for 20 minutes and a precipitate (triethylamine hydrochloride) appeared after one minute and this was filtered off. The solvent was evaporated and the residue diluted with water. The aqueous mixture was basified with 10% sodium carbonate solution and extracted with ethyl acetate. The organic phase was washed with brine, dried over $Na_2So_4$ and concentrated in vacuo to give 3.50 g of the desired base as a yellow-coloured oil. This was converted to the hydrochloride which was recrystallized from hot ethyl acetate/acetone to give 1.9 g of 3-acetoxy-1-methyl-4-(m-methylphenoxy)-4-phenyl-piperidine hydrochloride as a white solid having a melting point of 197°–9° C.

EXAMPLE 3

3-Hydroxy-1-methyl-4-phenyl-4-propionoxy-piperidine and its hydrochloride

A solution of 4.0 g of 3,4-epoxy-1-methyl-4-phenyl-piperidine and 4.5 g of p-toluenesulfonic acid monohydrate in 50 ml of propionic acid was stirred at room temperature for 10 minutes then the mixture evaporated to dryness. Water was added to the residue and the mixture made alkaline with sodium carbonate. The residual solid was filtered off and washed with water. Recrystallization of this solid from hot ethyl acetate gave 2.4 g of 3-hydroxy-1-methyl-4-phenyl-4-propionoxy-piperidine with a melting point of 142°–3° C. The corresponding hydrochloride salt had a melting point of 186°–8° C.

EXAMPLE 4

4-Ethoxy-3-hydroxy-1-methyl-4-phenyl-piperidine and its hydrochloride

A solution of 12 g (0.063 mole) of 3,4-epoxy-1-methyl-4-phenyl-piperidine and 14.4 g (0.075 mole) of p-toluenesulfonic acid monohydrate in 100 ml ethanol was refluxed for eight minutes. The solution was concentrated to 20 ml and then diluted with water. The aqueous solution was basified with 10% sodium hydroxide solution and extracted with ethyl acetate. The organic phase was washed with brine, dried over sodium sulfate and concentrated in vacuo to give 13.25 g of a beige solid. Recrystallization of the solid from hot ethanol gave 7.6 g of 4-ethoxy-3-hydroxy-1-methyl-4-phenyl-piperidine having a melting point of 145°–6° C.

Elementary Analysis: Calc: C: 71.45; H: 9.00; N: 5.95; Found: C: 71.25; H: 9.16; N: 5.86.

The corresponding hydrochloride salt, prepared in the usual manner, and recrystallized from acetone/isopropanol had a melting point of 205° C.

EXAMPLE 5

4-(t-Butylthio)-3-hydroxy-1-methyl-4-phenyl-piperidine and its hydrochloride 20 Ml of 10% sodium hydroxide solution was added to a solution of 5.4 ml (0.050 mole) of t-butylthiol in 40 ml of ethylene glycol and the resulting solution stirred at room temperature for 10 minutes, 3.8 G (0.02 mole) of 3,4-epoxy-1-methyl-4-phenyl-piperidine was added with stirring to the above solution and the resulting solution was heated at 100° C. (oil bath temperature) for three hours. A solid separated during the reaction period. The reaction mixture was cooled in an ice-bath, the solid filtered, washed with acetone and finally suspended in acetone and filtered. Recrystallization of this product from isopropanol/ether gave 3.2 g of the desired 4-(t-butylthio)-3-hydroxy-1-methyl-4-phenyl-piperidine as a white solid having a melting point of 202.5°–203° C.

The corresponding hydrochloride salt was prepared in the usual manner, crystallized from acetone/ethylacetate and was found to have a melting point of 222°–3° C.

EXAMPLE 6

3-Hydroxy-1-methyl-4-phenyl-1-phenylthio-piperidine and its hydrochloride 9.6 Ml of 10% sodium hydroxide solution was added to a solution of 2.46 ml (0.024 mole) of thiophenol in 15 ml of ethylene glycol and the resulting solution stirred at room temperature for five minutes. 1.9 G (0.01 mole) of 3,4-epoxy-1-methyl-4-phenyl-piperidine was added with stirring to the above solution and the resulting solution stirred at room temperature for a further one hour. A solid began to separate after five minutes. The solid was filtered and suspended in acetone. Filtration of the solid gave 2.6 g of 3-hydroxy-1-methyl-4-phenyl-4-phenylthio-piperidine as a white solid having a melting point of 217°–9° C.

Elementary Analysis: Calc: C: 64.36; H: 6.60; N: 4.17; Found: C: 64.33; H: 6.86; N: 4.02.

The corresponding hydrochloride was prepared in the usual manner and recrystallization from ethanol/ether gave colourless crystals of the hydrochloride salt having a melting point of 208.5°–210.5° C.

EXAMPLE 7

3-Acetoxy-1-methyl-4-(1-methyl-1-propanethio)-4-phenyl-piperidine and its hydrochloride 0.6 Ml (0.0077 mole) of acetyl chloride was added dropwise to a stirred solution of 1.8 g (0.0065 mole) of 3-hydroxy-1-methyl-4-(1-methyl-1-propanethio)-4-phenyl-piperidine in 25 ml of dry methylene chloride cooled in an ice-bath. The reaction mixture was stirred at room temperature for 20 minutes. The solvent was then removed in vacuo to give 2.0 g of a white solid. Recrystallization of the solid from acetone/isopropanol gave 1.3 g of 3-acetoxy-1-methyl-4-(1-methyl-1-propanethio)-4-phenyl-piperidine hydrochloride having a melting point of 214°–6° C.

Further compounds of Formula 1 according to the present invention are laid out in the following table, these compounds being prepared by the procedures detailed in the preceding Examples but with the appropriate changes in starting materials etc. These compounds all fall within the formula I wherein

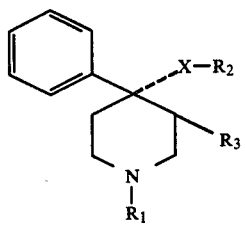

I

| Example | R₁ | R₂ | R₃ | X | M.P. (°C.) Base | M.P. (°C.) HCl Salt |
|---|---|---|---|---|---|---|
| 8 | —CH₃ | —⌬—OCH₃ | —OCOCH₃ | O | | 212-4 |
| 9 | —CH₃ | —⌬—CH₃ | —OH | O | | 221-2 |
| 10 | —CH₃ | —⌬ (cyclohexyl) | —OH | O | | 214-5 |
| 11 | —CH₃ | —⌬ (cyclohexyl) | —OCOCH₃ | O | | 240-1 |
| 12 | —CH₃ | —CH₃ | —OCOC(CH₃)₃ | O | | 230 |
| 13 | —CH₃ | —CH₂CH₃ | —OCOCH₃ | O | | 234-6 |
| 14 | —CH₃ | —CH₃ | —OCO—⌬ | O | | 205 |
| 15 | —CH₃ | —⌬ | —OH | O | 163-5 | 209-12 |
| 16 | —CH₃ | —⌬—Cl | —OH | O | 164-5 | |
| 17 | —CH₃ | —⌬ | —OCOCH₃ | O | | sublimes |
| 18 | —CH₃ | —⌬—Cl | —OCOC₂H₅ | O | | sublimes |
| 19 | —CH₃ | —CH₂CH₃ | —OH | O | 145-6 | |
| 20 | —CH₃ | —COCH₃ | —OCOCH₃ | O | | 254-5 |
| 21 | —CH₃ | —COC₂H₅ | —OCOCH₃ | O | | 199-200 |
| 22 | —CH₃ | —CH(CH₃)₂ | —OH | O | | 204-5 |
| 23 | —CH₃ | —CH(CH₃)₂ | —OCOCH₃ | O | | 250-1 |
| 24 | —CH₃ | 2,4-di-Cl-phenyl | —OH | O | | 243-5 |
| 25 | —CH₃ | —COCH₃ | —OH | O | | 228-9 |
| 26 | —CH₃ | —CH₃ | —OH | O | 135-7 | |
| 27 | —CH₃ | 2-Cl-phenyl | —OH | O | | 230-1 |
| 28 | —CH₃ | 2,4-di-Cl-phenyl | —OCOCH₃ | O | | 237-9 |

-continued

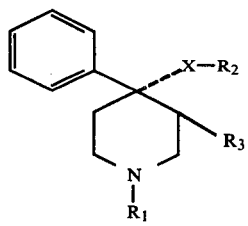

I

| Example | R₁ | R₂ | R₃ | X | M.P. (°C.) Base | M.P. (°C.) HCl Salt |
|---|---|---|---|---|---|---|
| 29 | —CH₃ | 2-Cl-C₆H₄— | —OCOCH₃ | O | | 238–40 |
| 30 | —CH₃ | 4-OCH₃-C₆H₄— | —OH | O | | 223–4.5 |
| 31 | —CH₃ | —CH₃ | —OCO-C₆H₄-NH₂ | O | | 225 |
| 32 | —CH₃ | —CH₃ | —OCO-C₆H₄-Cl | O | | 230–33 |
| 33 | —CH₃ | —CH₃ | —OCO-C₆H₄-NO₂ | O | | 255–8 |
| 34 | —CH₃ | —CH₃ | —OCO-(2-furyl) | O | | 225–8 |
| 35 | —CH₃ | —COEt | —OCO-C₆H₅ | O | | 239–41 |
| 36 | —CH₃ | —CH₃ | —OCOEt | O | | 237–9 |
| 37 | —CH₃ | —CH₃ | —OCOCH(Ph)₂ | O | | 249–50 |
| 38 | —CH₃ | —CH₃ | —OCOCH₃ | O | | 246–8 |
| 39 | —CH₃ | —CH₃ | —OCOC₂H₅ | O | | 224–5 |
| 40 | —CH₃ | —C₂H₅ | —OCOCH=CH₂ | O | | 215–7 |
| 41 | —CH₃ | —CH₃ | —OCO-cyclopropyl | O | | 263 |
| 42 | —CH₃ | 4-OCH₃-C₆H₄— | —OCOEt | O | | 217–8 |
| 43 | —CH₃ | 3,5-Cl₂-C₆H₃— | —OCOEt | O | | 231–2 |
| 44 | —CH₃ | —C₂H₅ | —OCO-cyclopropyl | O | | 215–7 |
| 45 | —CH₃ | —C₂H₅ | —OCO-C₆H₅ | O | | 183–5 |
| 46 | —CH₃ | 2-Cl-C₆H₄— | —OCOC₂H₅ | O | | 215–7 |
| 47 | —CH₃ | —COC₂H₅ | —OCO-cyclopropyl | O | | 195–7 |
| 48 | —CH₃ | —COC(CH₃)₃ | —OH | O | | 214–5 |
| 49 | —CH₃ | —CO-C₆H₅ | —OH | O | | 160–2 |
| 50 | —CH₃ | —CO-C₆H₅ | —OCOCH₃ | O | | 149–50 |
| 51 | —CH₃ | —CH₂—C≡CH | —OH | O | | 240–2 |

-continued

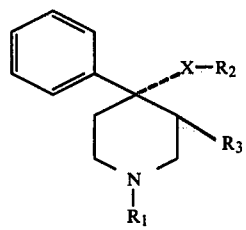

I

| Example | R₁ | R₂ | R₃ | X | M.P. (°C.) Base | M.P. (°C.) HCl Salt |
|---|---|---|---|---|---|---|
| 52 | —CH₃ | —CH₂—CH=CH₂ | —OH | O | | 175–6 |
| 53 | —CH₃ | —CH(CH₃)₂ via —CH(CH₃)CH₃ | —OCO—⊲ | O | | 230–1 |
| 54 | —CH₃ | —CH₃ | —OCO—C(CH₃)₂—O—C₆H₄—Cl | O | | 222–5 |
| 55 | —CH₃ | —CH₂—CH₂—OCH₃ | —OH | O | | 136–7 |
| 56 | —CH₃ | —CH(CH₃)CH₃ (isobutyl-type) | —OCO—C₆H₅ | O | | 235–7 |
| 57 | —CH₃ | —CH(CH₃)CH₃ | —OCOEt | O | | 171–3 |
| 58 | —CH₃ | —CH₃ | —OCO—C₆H₄—OCOCH₃ | O | | 210–11 |
| 59 | —CH₃ | —CH₂—C≡CH | —OCOEt | O | | 165–7 |
| 60 | —CH₃ | —CH₂—C≡CH | —OCO—C₆H₄—OCOCH₃ | O | | 223–4 |
| 61 | —CH₃ | —CH₂—C≡CH | —OCO—⊲ | O | | 195–6 |
| 62 | —CH₃ | —CH₂—CH₂—OCH₃ | —OCO—⊲ | O | | 200–2 |
| 63(a) | —CH₃ | —COCH₃ | —OCO—C₆H₂(OCH₃)₃ | O | | 181–2.5 |
| 63(b) | —CH₃ | —COC₂H₅ | —OCO—C₆H₂(OCH₃)₃ | O | | 84–6 |
| 64 | —CH₃ | —COCH₃ | —OCO—C₆H₁₁ | O | | 225–8 |
| 65 | —CH₃ | —COCH₃ | —OCO—C₆H₅ | O | | 206–8 |
| 66 | —CH₃ | —COCH₃ | —OCO—C₆H₄—Cl | O | | 226–8 |
| 67 | —CH₃ | —CH₃ | —OCO—C₆H₄—NH—COCH₃ | O | | 229–31 |
| 68 | —CH₃ | —CH₃ | —OCO—C₆H₄—CF₃ | O | | 211–3 |
| 69 | —CH₃ | —CH₂—CH₂—OCH₃ | —OCO—C₆H₅ | O | | 208–10 |

-continued

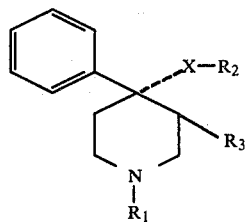
I

| Example | R₁ | R₂ | R₃ | X | M.P. (°C.) Base | M.P. (°C.) HCl Salt |
|---|---|---|---|---|---|---|
| 70 | —CH₃ | —COCH₃ | —OCO—cyclopropyl | O | | 235–7 |
| 71 | —CH₃ | —COCH₃ | —OCO—(2-furyl) | O | | 238–9 |
| 72 | —CH₂—Ph | —COCH₃ | —OH | O | | 234–5 |
| 73 | —CH₃ | —CH₂—CH₂—OCH₃ | —OCO—cyclohexyl | O | | 184–5 |
| 74 | —CH₃ | —COCH₃ | —OCOCH(Ph)(Ph) | O | | 101–3 |
| 75 | —CH₃ | —COCH₃ | —OCO—(2-OCOCH₃-phenyl) | O | | 202–4 |
| 76 | —CH₃ | —CO—C₂H₅ | —OCO—(2-furyl) | O | | 245–7 |
| 77 | —CH₃ | —COC₂H₅ | —OCO—(2-OCOCH₃-phenyl) | O | | 202–4 |
| 78 | —CH₃ | —CH₂CH₂—OCH₃ | —OCOCH₃ | O | | 202–4 |
| 79 | —CH₃ | —CH₂—CH₂—OCH₃ | —OCOC₂H₅ | O | | 188–9 |
| 80 | —CH₃ | —CH₂—CH₂—OCH₃ | —OCO—(2-OCOCH₃-phenyl) | O | | 134–6 |
| 81 | —CH₃ | —COC₂H₅ | —OCO—cyclohexyl | O | | 237–8 |
| 82 | —CH₃ | —CH₂—CH=CH₂ | —OCO—(2-OCOCH₃-phenyl) | O | | 184–7 |
| 83 | —CH₃ | —COC₂H₅ | —OCO—(4-Cl-phenyl) | O | | 215–7 |
| 84 | —CH₃ | —CH₂—CH=CH₂ | —OCO—phenyl | O | | 197–9 |
| 85 | —CH₃ | —CH₃ | —OCO—cyclohexyl | O | | 117–9 |
| 86 | —CH₃ | —CH₃ | —OCO—(2,3,4-triOCH₃-phenyl) | O | | 221–3 |
| 87 | —CH₃ | —CH(CH₃)(CH₃) | —OCO—(2-furyl) | O | | 208–10 |
| 88 | —CH₃ | —CH₂—C≡CH | —OCO—(2-furyl) | O | | 238 dec. |

-continued

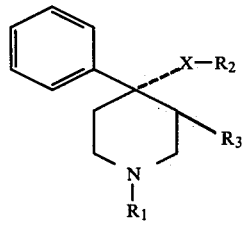

I

| Example | R₁ | R₂ | R₃ | X | M.P. (°C.) Base | HCl Salt |
|---------|-----|-----|-----|---|------|---------|
| 89 | —CH₃ | —CH₂—CH=CH₂ | —OCO—(furan) | O | | 217-8 |
| 90 | —CH₃ | —COC₂H₅ | —OCO—C(CH₃)₂—O—(4-Cl-phenyl) | O | | 199-201 |
| 91 | —CH₃ | —COC₂H₅ | —OCOC₂H₅ | O | | 171-3 |
| 92 | —CH₃ | —CH₂—C≡CH | —OCO—(phenyl) | O | | 241 |
| 93 | —CH₃ | —CH₂—CH=CH₂ | —OCO—(cyclopropyl) | O | | 207-9 |
| 94 | —CH₃ | —CH₂—C≡CH | —OCOCH₃ | O | | 205-7 |
| 95 | —CH₃ | —CH₂—CH=CH₂ | —OCO—CH=CH₂ | O | | 205-7 |
| 96 | —CH₂—CH₃ | —COC₂H₅ | —OH | O | | 178-180 |
| 97 | —CH₃ | —CH₂—C≡CH | —OCO—CH=CH₂ | O | | 213-5 |
| 98 | —CH₃ | —CH₂—CH=CH₂ | —OCOCH₃ | O | | 237-9 |
| 99 | —CH₃ | —COCH₃ | —OCO—(2,6-dimethoxyphenyl) | O | | 237 dec. (H₂SO₄ salt) |
| 100 | —CH₃ | —COC₂H₅ | —OCO—(cycloheptyl) | O | | 241-2 |
| 101 | —CH₃ | —COC₂H₅ | —OCO—(furan) | O | | 245-7 |
| 102 | —CH₃ | —COC₂H₅ | —OCO—(2-F-phenyl) | O | | 220-1 |
| 103 | —CH₃ | —CO—(cyclopropyl) | —OCOC₂H₅ | O | | 194-5 |
| 104 | —CH₃ | —COCH₃ | —OCO—(2,4-dimethylphenyl) | O | | 222-4 |
| 105 | —CH₃ | —COC₂H₅ | —OCO—(furan) | O | | 231-3 |
| 106 | —CH₃ | —COC₂H₅ | —OCO—(cyclobutyl) | O | | 182-5 dec. |
| 107 | —CH₃ | —COCH₃ | —OCO—(cyclopentyl) | O | | 235-6 |
| 108 | —CH₃ | —CO—(cyclopropyl) | —OCO—(cyclopropyl) | O | | 218-20 |
| 109 | —CH₃ | —COC₂H₅ | —OCO—(cyclopropyl) levo rotatory (specific rotation −48.4°) | O | | 221-2 |
| 110 | —CH₃ | COC₂H₅ | —OCO—(cyclopropyl) dextro rotatory (specific rotation +56.1°) | O | | 223-5 |

-continued

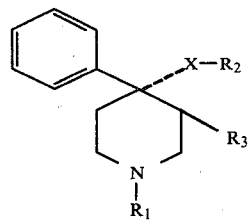

I

|  |  |  |  |  | M.P. (°C.) | |
|---|---|---|---|---|---|---|
| Example | R₁ | R₂ | R₃ | X | Base | HCl Salt |
| 111 | —CH₃ | —COC₂H₅ | —OCO—C₆H₃(CH₃)₂ (2,4-diMe) | O | 205–7 | |
| 112 | —CH₃ | —COCH₃ | —OCO—C₆H₃(CH₃)₂ (2,3-diMe) | O | 222–4 | |
| 113 | —CH₃ | —COCH₃ | —OCO—C₆H₃(CH₃)₂ (3,4-diMe) | | 241–3 (H₂SO₄ salt) | |
| 114 | —CH₃ | —COC₂H₅ | —OCO—C₆H₃(CH₃)₂ (3,4-diMe) | O | 218–9 (H₂SO₄ salt) | |
| 115 | —CH₃ | —COCH₃ | —OCO—C₆H₄—C(CH₃)₃ | O | 170–2 | |
| 116 | —CH₃ | —COC₂H₅ | —OCO—C₆H₄—CH₃ | O | 229–30 | |
| 117 | —CH₃ | —COCH₃ | —OCO—C₆H₄—CH₃ | O | 250 dec. | |
| 118 | —CH₃ | —COC₂H₅ | —OCO—C₆H₄—C₂H₅ | O | 217–9 | |
| 119 | —CH₃ | —COCH₃ | —OCO—C₆H₄—C₂H₅ | O | 222–3 | |
| 120 | —CH₃ | —COC₂H₅ | —OCO—C₆H₄—CH₃ (o-) | O | 211–3 | |
| 121 | —CH₃ | —COCH₃ | —OCO—C₆H₄—CH₃ (o-) | O | 234–6 | |
| 122 | —CH₃ | —COC₂H₅ | —OCO—C₆H₄—C(CH₃)₃ | O | 218–20 | |
| 123 | —CH₃ | —COC₂H₅ | —OCO—C₆H₄—CF₃ | O | 182–3 | |
| 124 | —CH₃ | —COCH₃ | —OCO—C₆H₄—CF₃ | O | 223–5 | |
| 125 | —CH₃ | —COC₂H₅ | —OCO—C₆H₄—OC₂H₅ | O | 217–9 (H₂SO₄ salt) | |
| 126 | —CH₃ | —COCH₃ | —OCO—C₆H₄—OC₂H₅ | O | 239–41 dec. (H₂SO₄ salt) | |

-continued

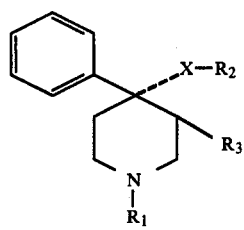

| Example | R₁ | R₂ | R₃ | X | M.P. (°C.) Base | HCl Salt |
|---|---|---|---|---|---|---|
| 127 | —CH₃ | —COC₂H₅ | —OCO—C₆H₃(OC₄H₉) | O | | 163–6 |
| 128 | —CH₃ | —COCH₃ | —OCO—C₆H₃(OC₄H₉) | O | | 212–4 |
| 129 | —CH₃ | —COC₂H₅ | —OCO—C₆H₄—O(CH₂)₂CH₃ | O | | 215–7 |
| 130 | —CH₃ | —COCH₃ | —OCO—C₆H₄—O(CH₂)₂CH₃ | O | | 238–9 (H₂SO₄salt) |
| 131 | —CH₃ | —COC₂H₅ | —OCO—C₆H₄(OC₂H₅) | O | | 204–5 |
| 132 | —CH₃ | —COCH₃ | —OCO—C₆H₄(OC₂H₅) | O | | 183–4 |
| 133 | —CH₃ | —COC₂H₅ | —OCO—C₆H₄—OC₂H₅ | O | | 208–10 |
| 134 | —CH₃ | —COCH₃ | —OCO—C₆H₄—OC₂H₅ | O | | 247–8 |
| 135 | —CH₃ | —COC₂H₅ | —OCO—C₆H₄(OCH₃) | O | | 227–8 (H₂SO₄salt) |
| 136 | —CH₃ | —COCH₃ | —OCO—C₆H₄(OCH₃) | O | | 209–10 |
| 137 | —CH₃ | —COC₂H₅ | —OCO—C₆H₃(OCH₃)(OCH₃) | O | | 241–2 |
| 138 | —CH₃ | —COCH₃ | —OCO—C₆H₃(OCH₃)(OCH₃) | O | | 208–9 |
| 139 | —CH₃ | —COC₂H₅ | —OCO—C₆H₃(OCH₃)(OCH₃) | O | | 232–3 |
| 140 | —CH₃ | —COC₂H₅ | —OCO—C₆H₄—OCH₃ | O | | 108–200 |
| 141 | —CH₃ | —COCH₃ | —OCO—C₆H₄—O(CH₂)₅CH₃ | O | | 205–6 |
| 142 | —CH₃ | —COC₂H₅ | —OCO—C₆H₄—O(CH₂)₄CH₃ | O | | 185–8 |
| 143 | —CH₃ | —COCH₃ | —OCO—C₆H₄—O(CH₂)₄CH₃ | O | | 175–7 |

-continued

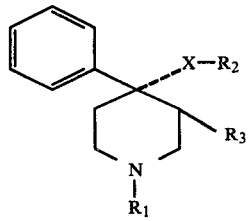

| Example | R₁ | R₂ | R₃ | X | M.P. (°C.) Base | HCl Salt |
|---|---|---|---|---|---|---|
| 144 | —CH₃ | —COC₂H₅ | —OCO—⟨phenyl⟩—O(CH₂)₃CH₃ | O | | 195-7 |
| 145 | —CH₃ | —COCH₃ | —OCO—⟨phenyl⟩—O(CH₂)₃CH₃ | O | | 227-9 |
| 146 | —CH₃ | —⟨phenyl⟩ | —OCOC₂H₅ | S | | 198-201 |
| 147 | —CH₃ | —⟨o-Cl-phenyl⟩ | —OH | S | | 223-8 |
| 148 | —CH₃ | —⟨o-Cl-phenyl⟩ | —OCOCH₃ | S | | 202-5 |
| 149 | —CH₃ | —CH(CH₃)—CH₂—CH₃ | —OH | S | | 183-5 |
| 150 | —CH₃ | —C(CH₃)₃ | —OCOCH₃ | S | | 233-4 |
| 151 | —CH₃ | —⟨phenyl⟩ | —OCOC₂H₅ | S | | 198-201 |

Basic elemental analysis of some compounds of the above examples is contained in the following table:

TABLE

| | C | H | N |
|---|---|---|---|
| Example 3 | | | |
| Calculated: | 67.10 | 6.97 | 3.73 |
| Found: | 66.86 | 7.33 | 3.98 |
| Example 8 | | | |
| Calculated: | 64.36 | 6.69 | 3.58 |
| Found: | 64.41 | 6.78 | 3.66 |
| Example 9 | | | |
| Calculated: | 68.35 | 7.25 | 4.20 |
| Found: | 68.57 | 7.09 | 4.16 |
| Example 16 | | | |
| Calculated: | 68.02 | 6.34 | 4.41 |
| Found: | 68.10 | 6.62 | 4.34 |
| Example 19 | | | |
| Calculated: | 71.45 | 9.00 | 5.95 |
| Found: | 71.25 | 9.16 | 5.87 |
| Example 24 | | | |
| Calculated: | 55.61 | 5.19 | 3.60 |
| Found: | 55.55 | 5.40 | 3.53 |
| Example 27 | | | |
| Calculated: | 61.02 | 5.98 | 3.95 |
| Found: | 61.12 | 6.14 | 4.10 |
| Example 30 | | | |
| Calculated: | 65.42 | 6.65 | 4.02 |
| Found: | 65.82 | 6.83 | 4.23 |
| Example 40 | | | |
| Calculated: | 62.66 | 7.42 | 4.30 |
| Found: | 62.72 | 7.63 | 4.18 |
| Example 52 | | | |
| Calculated: | 72.84 | 8.56 | 5.66 |
| Found: | 72.63 | 8.51 | 5.73 |

TABLE-continued

| | C | H | N |
|---|---|---|---|
| Example 54 | | | |
| Calculated: | 60.86 | 6.44 | 3.09 |
| Found: | 60.66 | 6.61 | 3.28 |
| Example 71 | | | |
| Calculated: | 61.27 | 6.57 | 3.97 |
| Found: | 61.34 | 6.70 | 4.14 |
| Example 76 | | | |
| Calculated: | 60.99 | 6.14 | 3.56 |
| Found: | 61.02 | 6.28 | 3.74 |
| Example 81 | | | |
| Calculated: | 64.45 | 7.87 | 3.42 |
| Found: | 64.12 | 8.09 | 3.62 |

The detailed preparation of representative 3,4-epoxypiperidines which are used as starting materials in many of the specific examples contained in this specification are as follows:

(a) 3,4-Epoxy-4-phenyl-piperidine

A solution of 33.6 g of bromine and 60 g of sodium bromide in 450 ml of water was added dropwise with stirring to solution comprising 50 g of 4-phenyl-1,2,5,6-tetrahydropyridine hydrobromide in 600 ml of water and the reaction mixture was then stirred at room temperature for 30 minutes. The solution was stirred on an ice bath while 252 ml of 10% sodium hydroxide was added dropwise thereto. The resulting mixture then being stirred at room temperature for a further 30 minutes. The aqueous solution was extracted with methylene chloride and the organic phase solution dried over sodium sulfate and then concentrated in vacuo to give 25.2 g of the desired 3,4-epoxy-4-phenyl piperidine as an oil.

(b) 1-Benzyl-3,4-epoxy-4-phenyl-piperidine 22.5 Ml of benzyl bromide was added dropwise to a stirred solution of 32.3 g of 3,4-epoxy-4-phenylpiperidine and 38.1 ml of triethylamine in 254 ml of benzene. A precipitate appeared during the addition. The whole reaction mixture was then stirred at room temperature for three hours. The residual solid was removed by filtration and the solvent evaporated to give 53.4 g of 1-benzyl-3,4-epoxy-4-phenyl-piperidine.

We claim:

1. A 4-phenyl piperidine having the formula:

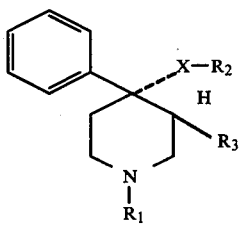

wherein $R_1$ is a straight chain lower alkyl group;

$R_2$ is —COCH$_3$, —COC$_2$H$_5$ or

$R_3$ is —OCOCH$_3$, —OCOC$_2$H$_5$, —OCO-cycloalkyl, or —OCOC$_6$H$_4$—Z;

wherein Z is hydrogen, lower alkyl, lower alkoxy or chlorine, and X is oxygen; or an addition salt thereof with a pharmaceutically acceptable organic acid or inorganic acid.

2. A compound as claimed in claim 1 which is 1-methyl-3-cyclopropylcarbonyloxy-4-ethylcarbonyloxy-4-phenyl-piperidine or a pharmaceutically acceptable acid addition salt thereof with an organic acid or inorganic acid.

3. A compound as claimed in claim 1 which is 1-methyl-3-ethylcarbonyloxy-4-ethylcarbonyloxy-4-phenyl-piperidine or a pharmaceutically acceptable acid addition salt thereof with an organic acid or inorganic acid.

4. A compound as claimed in claim 1 which is 1-methyl-3-phenylcarbonyloxy-4-ethylcarbonyloxy-4-phenyl-piperidine or a pharmaceutically acceptable acid addition salt thereof with an organic acid or inorganic acid.

5. A compound as claimed in claim 1 which is 1-methyl-3-acetoxy-4-ethylcarbonyloxy-4-phenyl-piperidine or a pharmaceutical acceptable acid addition salt thereof with an organic acid or inorganic acid.

6. 1-methyl-3-(2',6'-dimethoxy-phenylcarbonyloxy)-4-acetoxy-4-phenyl-piperidine or a pharmaceutically acceptable acid addition salt thereof with an organic acid or inorganic acid.

7. A compound as claimed in claim 1 which is 1-methyl-3-cycloheptylcarbonyloxy-4-ethylcarbonyloxy-4-phenylpiperidine or a pharmaceutically acceptable acid addition salt thereof with an organic acid or inorganic acid.

8. 1-methyl-3-(2'-furylcarbonyloxy)-4-ethylcarbonyloxy-4-phenyl-piperidine or a pharmaceutically acceptable acid addition salt thereof with an organic acid or inorganic acid.

9. 1-methyl-3-(2'-fluorophenylcarbonyloxy)-4-ethylcarbonyloxy-4-phenyl-piperidine or a pharmaceutically acceptable acid addition salt thereof with an organic acid or inorganic acid.

10. A compound as claimed in claim 1 which is 1-methyl-3-ethylcarbonyloxy-4-cyclopropylcarbonyloxy-4-phenyl-piperidine or a pharmaceutically acceptable acid addition salt thereof with an organic acid or inorganic acid.

* * * * *